United States Patent
Baskis

(10) Patent No.: US 9,895,404 B1
(45) Date of Patent: Feb. 20, 2018

(54) CANNABIDIOL EXTRACTION PLANT AND PROCESSES

(71) Applicant: Paul T. Baskis, Oakland, KY (US)

(72) Inventor: Paul T. Baskis, Oakland, KY (US)

( * ) Notice: Subject to any disclaimer, the term of this patent is extended or adjusted under 35 U.S.C. 154(b) by 36 days.

(21) Appl. No.: 15/290,187

(22) Filed: Oct. 11, 2016

Related U.S. Application Data

(60) Provisional application No. 62/239,476, filed on Oct. 9, 2015.

(51) Int. Cl.
- *A61K 36/185* (2006.01)
- *A61K 31/352* (2006.01)
- *A61K 31/05* (2006.01)

(52) U.S. Cl.
CPC ............ *A61K 36/185* (2013.01); *A61K 31/05* (2013.01); *A61K 31/352* (2013.01); *A61K 2236/15* (2013.01); *A61K 2236/33* (2013.01); *A61K 2236/51* (2013.01); *A61K 2236/55* (2013.01)

(58) Field of Classification Search
CPC .................................................. A61K 2236/55
See application file for complete search history.

(56) References Cited

FOREIGN PATENT DOCUMENTS

WO      WO2014200350 A1 * 12/2014

\* cited by examiner

*Primary Examiner* — Noble Jarrell
*Assistant Examiner* — John S Kenyon
(74) *Attorney, Agent, or Firm* — Nixon Peabody LLP

(57) ABSTRACT

A method for extracting cannabinoids from plant material containing one or more cannabinoids including: (1) shredding the plant material into an appropriate size; (2) soaking the shredded plant material in a polar solvent to dissolve the one or more cannabinoids into the alcohol to form a polar solvent/cannabinoid mixture; (3) separating the polar solvent/cannabinoid mixture from residual solid plant material; (4) treating the polar solvent/cannabinoid mixture to a non-polar solvent to remove the one or more cannabinoids into the non-polar solvent to form a non-polar solvent/cannabinoid mixture; (5) distilling the non-polar solvent/cannabinoid mixture to separate the non-polar solvent from the one or more cannabinoids; and (6) subjecting the cannabinoid mixture to a supercritical fluid to isolate and purify the cannabinoid mixture into individual cannabinoids of the one or more cannabinoids.

6 Claims, 1 Drawing Sheet

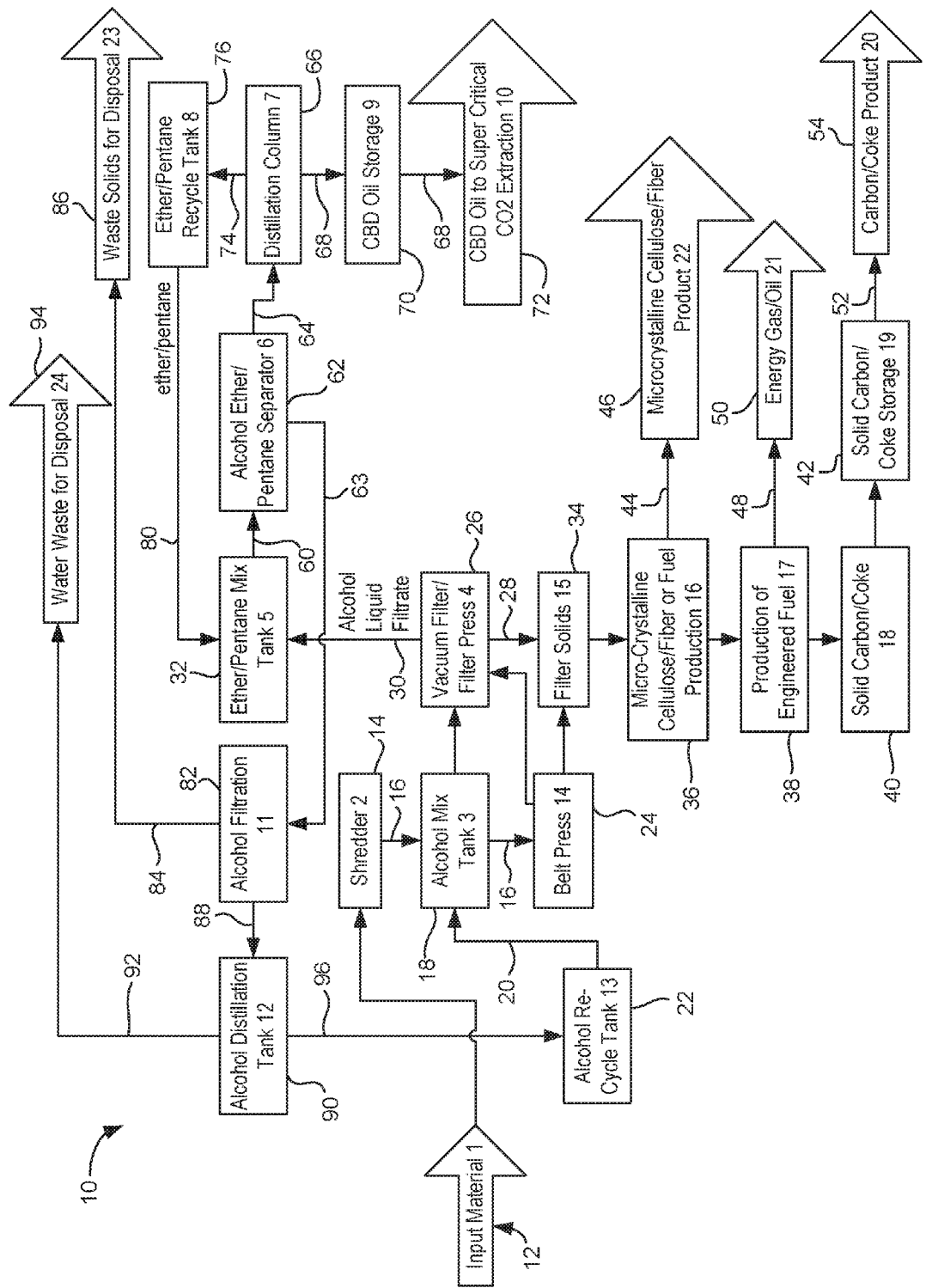

CANNABIDIOL EXTRACTION PLANT AND PROCESSES

CROSS-REFERENCE TO RELATED APPLICATIONS

The present invention claims the benefit of U.S. Provisional Patent Application No. 62/239,476 filed Oct. 9, 2015, the contents of which are incorporated herein by reference.

FIELD OF THE INVENTION

Disclosed herein is a process and plant for extracting cannabinoids and other essential alkaloid oils from plants containing these compounds.

BACKGROUND OF THE INVENTION

There are a variety of cannabinoid compounds that are contained in plants such as marijuana and industrial hemp and can be extracted therefrom. Three well-studied cannabinoids include tetrahydrocannabinol (THC), cannabidiol (CBD) and cannabinol (CBN). Common methods for extracting cannabinoid compounds from phytocannabinoid plants include solvent extraction using hydrocarbons and alcohols, butane, and supercritical fluid carbon dioxide. Once separated from the plants, cannabinoid blends can be separated into individual compounds. Cannabidiol is not psychoactive, is not a controlled substance and is available for legal purchase and use without prescription in the United States. CBD is reported to relieve convulsions, anxiety, nausea and inflammation.

BRIEF DESCRIPTION OF THE DRAWINGS

To understand the present invention, it will now be described by way of example, with reference to the accompanying FIGURES in which:

FIG. 1 is a schematic representation of a flow-through process and plant for extracting cannabinoids from plants.

DETAILED DESCRIPTION

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

FIG. 1 shows a layout of a plant 10 for extracting cannabinoids from plants containing such compounds. Industrial hemp and marijuana refer to the same plant Cannabis Sativa. Industrial hemp has a THC content of less than 1.5% and marijuana has a THC content greater than 1.5%. In a preferred form of the invention, the process is continuous as opposed to a batch process. Suitable plant material, such as industrial hemp, is input 12 into the plant and conveyed to a shredder 14 where it is reduced to an appropriate size. The process allows for the use of plant material freshly harvested from a field or other growing facility and without first drying the material. In a preferred form of the invention, the shredder is operated at low speeds to keep from forming excess heat which might damage or denature the desired compounds being extracted. During the shredding process, resinous materials accumulate and can slow the cutting blades of the shredder. The amperage of the motor that turns the shredding blades is monitored and when the amperage levels reach a set point, an alcohol or other suitable solvent is sprayed on or otherwise delivered to the blades to clean them.

The solid shredded material 16 is delivered from the shredder 12 to a first alcohol mix tank 18 which receives alcohol 20 from a source location such as an alcohol recycle tank 22. The material 16 is allowed to reside in the tank for an effective period of time and is then conveyed to a belt press 24 or a vacuum filter 26 to separate the spent plant material 28 from the alcohol and cannabinoid mixture 30. The first alcohol step eliminates waxes that are a contaminate problem in the $CO_2$ extraction step discussed below and when the alcohol is removed from the mix to determine the CBD content at this point in the process it was found the resulting product was an oil with 55% to 60% CBD concentration.

The alcohol/cannabinoid mixture 30 is conveyed to a mix tank 32 containing a mixture of petroleum ether or pentane or other non polar solvent where it is thoroughly mixed. The spent plant material 28 having the majority of alcohol removed is sent to a surge tank 34 for the filter of solids and the filter solids 36 are transferred to a system for preparing and separating the microcrystalline cellulose utilizing a claflin refiner or similar equipment 36 where microcrystalline cellulose 44 is isolated in 36 and sent to storage 46, or the fiber can be sent to a coal to oil process 38 where some of the engineered fuel is liquid and gas 48 and is conveyed to a storage unit 50 or for immediate use in the plant, and solid coke 40 is transferred to a solid coke storage 42.

After the alcohol/cannabinoid mixture 30 has resided in the petroleum ether/alcohol tank 32, the mixture 60 is conveyed to a separation tank 62 where the polar solvent, alcohol 63, is separated from the non-polar solvents such as pentane or petroleum ether 64 which now contain the base cannabinoid oil compounds of interest. To determine the CBD concentration at this point, CBD base oil is separated by distillation 66 and a sample taken from the distillation 66 and is found to have a CBD concentration as high as 90%

The pentane/petroleum ether/cannabinoids mixture 64 is conveyed to a distillation column 66 where the cannabinoid compounds 68 are conveyed to a storage tank 70 and then to a supercritical fluid extraction unit 72 to isolate and purify CBD oil for sale and use. The first two extraction steps yield a product that can be processed in a flow-through process at high pressures which could not otherwise be used processing solids such as stems and leaves.

A petroleum ether or pentane 74 is conveyed from the distillation column 66 to a recycle tank 76 and a distilled compound of non-polar solvents such as petroleum ether or pentane 80 is conveyed back to the mix tank 32 and then to the separation tank 62.

The alcohol portion 63 from the separation tank 62 is conveyed to a filter 82 where solid waste materials 84 are separated and conveyed to a waste solids disposal 86. A purified alcohol 88 is conveyed to an alcohol distillation tank 90 where the alcohol is concentrated through distillation and the water fraction 92 is conveyed to a water waste disposal location 94 and the concentrated alcohol fraction 96 is conveyed to the alcohol recycle tank 22.

A method for extracting cannabinoids from plant material includes the steps of: (1) shredding the plant material into an appropriate size, (2) soaking the shredded plant material in a polar solvent such as alcohol to dissolve the cannabinoids into the polar solvent to form a polar solvent/cannabinoid mixture, (3) separating the polar solvent/cannabinoid mixture from residual solid plant material and waxes that when sampled yield an oil having a CBD concentration of 55% to about 60%, (4) treating the polar solvent/cannabinoid mixture to a non-polar solvent or a combination of non-polar solvents (e.g., petroleum ether and or pentane) to remove the cannabinoid compounds into the non-polar solvent(s), the mixture when sampled yields a CBD oil with a CBD content from about 80% to 90%, (5) distilling the non-polar solvent(s)/cannabinoid mixture to separate the non-polar solvents from the cannabinoids, and (6) subjecting the cannabinoid mixture to a supercritical fluid carbon dioxide to isolate and purify the cannabinoids. In a preferred form of the invention, the supercritical fluid carbon dioxide step is carried out as a flow-through process at high pressures normally used for supercritical fluid carbon dioxide extraction. In a preferred form of the invention where industrial hemp is used as the plant material, CBD oil is isolated and purified. However, if marijuana plant is used THC, CBD, CBN and other cannabinoids can be separated and purified.

Suitable polar solvents include alcohols, aldehydes, ketones, carboxylic acids and mixtures of the same, for example. In a more preferred form of the invention, the polar solvent is an alcohol having from two to eight carbons and most preferably is ethanol.

Suitable non-polar solvents include petroleum ether, alkanes and mixtures of the same. Suitable petroleum ethers include petroleum fractions of a mixture of $C_5$ and $C_6$ hydrocarbons boiling in the range of 35-60° C. Suitable alkanes include those having from two to eight carbons and more preferably from three to six carbons and most preferably is pentane. A preferred combination of non-polar solvents includes petroleum ether and pentane.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

I claim:

1. A method for extracting cannabinoids from plant material containing one or more cannabinoids comprising:
   (1) shredding the plant material into an appropriate size;
   (2) soaking the shredded plant material in a polar solvent to dissolve the one or more cannabinoids into the polar solvent to form a polar solvent/cannabinoid mixture;
   (3) separating the polar solvent/cannabinoid mixture from residual solid plant material;
   (4) treating the polar solvent/cannabinoid mixture to a non-polar solvent to remove the one or more cannabinoids into the non-polar solvent to form a non-polar solvent/cannabinoid mixture;
   (5) distilling the non-polar solvent/cannabinoid mixture to separate the non-polar solvent from the one or more cannabinoids; and
   (6) subjecting the cannabinoid mixture to a supercritical fluid to isolate and purify the cannabinoid mixture into individual cannabinoids of the one or more cannabinoids.

2. The method of claim 1 wherein the polar solvent is selected from the group consisting of alcohols, aldehydes, ketones, carboxylic acids and mixtures of the same.

3. The method of claim 1 wherein the non-polar solvent is selected from the group consisting of petroleum ether, alkanes and mixtures of the same.

4. The method of claim 1 wherein the plant material is Cannabis Sativa.

5. The method of claim 1 wherein the cannabinoid is selected from the group consisting of tetrahydrocannabinol (THC), cannabidiol (CBD) and cannabinol (CBN).

6. The method of claim 1 wherein the method further comprises the step of obtaining the plant material directly from the field without drying.

* * * * *